US007015012B2

(12) United States Patent
Housman et al.

(10) Patent No.: US 7,015,012 B2
(45) Date of Patent: Mar. 21, 2006

(54) METHODS OF IDENTIFYING AGENTS THAT MEDIATE POLYPEPTIDE AGGREGATION

(75) Inventors: David E. Housman, Newton, MA (US); Aleksey G. Kazantsev, Brighton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/470,765

(22) PCT Filed: Feb. 11, 2002

(86) PCT No.: PCT/US02/04059

§ 371 (c)(1),
(2), (4) Date: Mar. 23, 2005

(87) PCT Pub. No.: WO02/064618

PCT Pub. Date: Aug. 22, 2002

(65) Prior Publication Data

US 2005/0221272 A1    Oct. 6, 2005

Related U.S. Application Data

(60) Provisional application No. 60/267,815, filed on Feb. 9, 2001.

(30) Foreign Application Priority Data

Feb. 11, 2002  (WO) ...................... PCT/US02/04059

(51) Int. Cl.
    *C12Q 1/02*  (2006.01)
(52) U.S. Cl. .......................................... 435/29; 435/35
(58) Field of Classification Search ...................... None
    See application file for complete search history.

(56) References Cited

U.S. PATENT DOCUMENTS

| 5,144,011 A | 9/1992 | Shen et al. |
|---|---|---|
| 5,328,470 A | 7/1994 | Nabel |
| 5,849,995 A | 12/1998 | Hayden |
| 5,994,392 A | 11/1999 | Shashoua |
| 6,015,555 A | 1/2000 | Friden |
| 6,177,259 B1 | 1/2001 | Yuan |
| 6,355,690 B1 | 3/2002 | Tsuji |

FOREIGN PATENT DOCUMENTS

WO     WO 01/23412     4/2001

OTHER PUBLICATIONS

Ambrose et al., "Structure and Expression of the Huntington's Disease Gene: Evidence against Simple Inactivation Due to an Expanded CAG Repeat," *Somat. Cell Mol. Genet.*20:27-38 (1994).

Bates et al., "Transgenic Mice in the Study of Polyglutamine Repeat Expansion Diseases," *Brain Pathol.*8:699-714 (1998).
Burright et al., "SCAI Transgenic Mice: A Model for Neurodegeneration Caused by an Expanded CAG Trinucleotide Repeat," *Cell*82:937-948 (1995).
Chen et al., "Gene Therapy for Brain Tumors: Regression of Experimental Gliomas by Adenovirus-Mediated Gene Transfer In Vivo," *Proc. Natl. Acad. Sci. USA*91:3054-3057 (1994).
Chicurel et al., "Expression of Huntington's Disease Mutation in Mice," at http://www.hdfoundation.org/PDF/hdmicetable.pdf (2000).
Cruikshank et al., "A Lipidated Anti-Tat Antibody Enters Living Cells and Blocks HIV-1 Viral Replication," *J. Acquired Immune Deficiency Syndromes and Human Retrovirology*14:193-203 (1997).
Davies et al., "Formation of Neuronal Intranuclear Inclusions Underlies the Neurological Dysfunction in Mice Transgenic for the HD Mutation," *Cell*90:537-548 (1997).
DiFiglia et al., "Aggregration of Huntingtin in Neuronal Intranuclear Inclusions and Dystrophic Neurites in Brain," *Science*277:1990-1993 (1997).
Duyao et al., "Inactivation of the Mouse Huntington's Disease Gene Homolog Hdh," *Science*269:407-410 (1995).
Gatter et al., "Transferrin Receptors in Human Tissues: Their Distribution and Possible Clinical Relevance," *J. Clin. Path.*36:539-545 (1983).
Gavilondo-Cowley et al., "Specific Amplification of Rearranged Immunoglobulin Variable Region Genes from Mouse Hybridoma Cells," *Hybridoma*9:407-417 (1990).
Goldstein et al., "Science and the Citizen," *Scientific American*255:74-91 (1996).
Gutekunst et al., "Nuclear and Neuropil Aggregates in Huntinton's Disease: Relationship to Neuropathology," *J. Neurosci.*19:2522-2534 (1999).
Haynes et al., "Characterization of a Monoclonal Antibody (5E9) that Defines a Human Cell Surface Antigen of a Cell," *J. Immunol.*127:347-351 (1981).

(Continued)

*Primary Examiner*—Terry McKelvey
(74) *Attorney, Agent, or Firm*—Fish & Richardson P.C.

(57) ABSTRACT

The present invention is based, in part, on the discovery of methods for identifying compounds that mediate (by promoting or inhibiting) protein-protein interaction (e.g., aggregation, dimerization, or other physiologically significant association). Compounds that mediate such interaction, which are also within the scope of the invention, can be used to treat Alzheimer's disease, disorders associated with expanded CAG repeats (such as Huntington's disease), and disorders in which polyglutamine-containing transcription factors or coactivators are undesirably active (e.g., disorders associated with homodimerization of jun or hexamerization of p53.

1 Claim, 3 Drawing Sheets

OTHER PUBLICATIONS

Hodgson et al., "A YAC Mouse Model for Huntington's Disease with Full-Length Mutant Huntingtin, Cytoplasmic Toxicity, and Selective Striatal Neurodegeneration," *Neuron* 23:181-192 (1999).

Hogan et al., *Manipulating the Mouse Embryo*, Cold Spring Harbor Laboratory Press, Cold Spring Harbor, New York (1994).

Ikeda et al., "Expanded Polyglutamine in the Machado-Joseph Disease Protein Induces Cell Death *In Vitro* and *In Vivo*," *Nature Genet.* 13:196-202 (1996).

Kakizuka, "Protein Precipitation: A Common Etiology in Neurodegenerative Disorders?," *Trends Genet.* 14:396-402 (1998).

Kazantsev et al., "Insoluble Detergent-Resistant Aggregates Form Between Pathological and Nonpathological Lengths of Polyglutamine in Mammalian Cells," *Proc. Natl. Acad. Sci. USA* 96:11404-11409 (1999).

Klement et al., "Ataxin-1 Nuclear Localization and Aggregation: Role in Polyglutamine-Induced Disease in *SCAI* Transgenic Mice," *Cell* 95:41-53 (1998).

Larrick et al., "Polymerase Chain Reaction Using Mixed Primers: Cloning of Human Monoclonal Antibody Variable Region Genes from Single Hybridoma Cells," *Bio/technology* 7:934-938 (1989).

Lebman et al., "A Monoclonal Antibody that Detects Expression of Transferrin Receptor in Human Erythroid Precursor Cells," *Blood* 59:671-678 (1982).

Li et al., "Ultrastructural Localization and Progressive Formation of Neuropil Aggregates in Huntington's Disease Transgenic Mice," *Hum. Mol. Getter.* 8:1227-1236 (1999).

Mangiarini et al., "Exon 1 of the HD Gene with an Expanded CAG Repeat is Sufficient to Cause a Progressive Neurological Phenotype in Transgenic Mice," *Cell* 87:493-506 (1996).

Omary et al., "Human Cell-Surface Glycoprotein with Unusual Properties," *Nature* 286:888-891 (1980).

Onodera et al., "Oligomerization of Expanded Polyglutamine Domain Fluorescent Fusion Proteins in Cultured Mammalian Cells," *Biochemical and Biophysical Research Communications*, 238:599-605 (1977).

Orlandi et al., "Cloning Immunoglobulin Variable Domains for Expression by the Polymerase Chain Reaction," *Proc. Nat. Acad. Sci. USA* 86:3833-3837 (1989).

Pardridge et al., "Receptor-Mediated Peptide Transport through the Blood-Brain Barrier," *Endocrin. Rev.* 7:314-330 (1986).

Paulson et al., "Protein Fate in Neurodegenerative Proteinopathies: Polyglutamine Diseases Join the (Mis) Fold," *Am. J. Hum. Genet.* 64:339-345 (1999).

Perutz et al., "Glutamine Repeats and Neurodegenerative Diseases: Molecular Aspects," *Trends Biochem. Sci.* 24:58-63 (1999).

Reddy et al., "Recent Advances in Understanding the Pathogenesis of Huntington's Disease," *Trends Neuroscience* 22:248-255 (1999).

Ross et al., "Intranuclear Neuronal Inclusions: A Common Pathogenic Mechanism for Glutamine-Repeat Neurodegenerative Diseases," *Neuron* 19:1147-1150 (1997).

Saudou et al., "Huntingtin Acts in the Nucleus to Induce Apoptosis but Death Does Not Correlate with the Formation of Intranuclear Inclusions," *Cell* 95:55-66 (1998).

Scherzinger et al., "Self-Assembly of Polyglutamine-Containing untingtin Fragments into Amyloid-Like Fibrils: Implications for Huntington's Disease Pathology," *Proc. Natl. Acad. Sci. USA* 96;4604-4609 (1999).

Sutherland et al., "Ubiquitous Cell-Surface Glycoprotein on Tumor Cells is Proliferation-Associated Receptor for Transferrin," *Proc. Natl. Acad. Sci. USA* 78:4515-4519 (1981).

Zeitlin et al., "Increased Apoptosis and Early Embryonic Lethality in Mice Nullizygous for the Huntington's Disease Gene Homologue," *Nature Genet.* 11:155-163 (1995).

Zhuchenko et al., "Autosomal Dominant Cerebellar Ataxia (SCA6) Associated with Small Polyglutamine Expansions in the - Voltage-Dependent Calcium Channel," *Nature* 15:62-69 (1997).

METHODS OF IDENTIFYING AGENTS THAT MEDIATE POLYPEPTIDE AGGREGATION

CROSS-REFERENCES TO RELATED APPLICATIONS

This application claims benefit of U.S. Provisional Application No. 60/267,815, filed Feb. 9, 2001.

STATEMENT AS TO FEDERALLY SPONSORED RESEARCH

The invention was made with Government support from the National Institutes of Health NIH Grant No. NIH-5P01-CA42063. The Government therefore has certain rights in this invention.

TECHNICAL FIELD

This invention relates to methods of identifying agents that mediate polypeptide aggregation, more particularly, agents that promote or inhibit the formation of aggregates that contain polyglutamine-rich polypeptides. Particular agents and their use in treating disease are also described.

BACKGROUND

At least eight progressive, inherited neurodegenerative disorders are caused by an expansion of the naturally occurring CAG tract that codes for a polyglutamine (polyQ) repeat within the coding region of the corresponding protein. These diseases include Huntington's disease (HD), spinal and bulbar muscular atrophy (SBMA; also known as Kennedy's disease), dentatorubral-pallidoluysian atrophy, spinocerebellar ataxia type 1 (SCA1), SCA2, SCA6, SCA7, and Machado-Joseph disease (MJD/SCA3)(Reddy et al. Trends Neuroscience 22:248–255, 1999). With the exception of SCA6 (CACNL1A4)(Zhuchenko et al. Nature 15:62–69, 1997), which is characterized by a minimal repeat expansion, affected individuals show a similar range of repeat expansion above ~35 repeats (Kakizukca et al. Trends Genet. 14:396–402, 1998).

Each disorder is inherited as an autosomal dominant (or X-linked in the case of SBMA), neurological syndrome with selective, neuronal cell death resulting in distinct, but overlapping, clinical and pathological manifestations (Ross et al. Neuron 19:1147–1150, 1997). Age of onset is normally in mid-life; however, longer repeat ranges can cause more severe presentation of the disease with an earlier age of onset. Genetic studies provide evidence that inactivation of a single allele does not result in disease (Duyao et al. Science 269:407–410, 1995; Zeitlin et al. Nature Genet. 11:155–163, 1995). In addition, mouse models for HD, SCA-1 and MJD (Reddy et al. Trends Neuroscience 22:248–255, 1999; Burright et al. Cell 82:937–948, 1995; Hodgson et al. Neuron 23:181–192, 1999; Ikeda et al. Nature Genet. 13:196–202, 1996; and Mangiarini et al. Cell 87:493–506, 1996), carrying expanded repeat transgenes in a background with two normal alleles, show phenotypes resembling the corresponding disease suggesting a true dominant effect. The appearance of neuronal intranuclear inclusions that contain huntingtin and ubiquitin, in mice transgenic for exon 1 of huntingtin, implicates protein misfolding and aggregation as potential mediators of neuronal pathogenesis (Davies et al. Cell 90:537–548, 1997). These insoluble neuronal aggregates and nuclear inclusions have been described for many of the polyQ repeat diseases, having been seen in the affected regions of brains from patients (Kakizuka et al. Trends Genet. 14:396–402, 1998; DiFiglia et al. Science 277:1990–1993, 1997; Bates et al. Brain Pathol. 8:699–714, 1998; Paulson et al. Am. J. Hum. Genet. 64:339–345, 1999) and in most of the transgenic mouse models (Bates et al. Brain Pathol. 8:699–714, 1998; Paulson et al. Am. J. Hum. Genet. 64:339–345, 1999).

A role for nuclear localization of expanded polyQ repeat-containing disease proteins, independent of aggregation, has also been implicated in the initiation of disease and neurodegeneration (Klement et al. Cell 95:41–53, 1998; Saudou et al. Cell 95:55–66, 1998). In contrast, the presence of cytosolic aggregates in dystrophic neurites and neuropils in HD brain sections and in HD transgenic mice may reflect a pathogenic role for non-nuclear localization and aggregation (DiFiglia et al. Science 277:1990–1993, 1997; Gutekunst et al. J. Neurosci. 19:2522–2534, 1999; Li et al. Hum. Mol. Getter. 8:1227–1236, 1999). The aggregation phenomenon has been reproduced in vitro in a protein concentration and repeat length-dependent manner (Scherzinger et al. Proc. Natl. Acad. Sci. USA 96:4604–4609, 1999), demonstrating that aggregation is a property mediated by the expanded polyQ. The structure and behavior of polyQ repeats, both isolated and in protein contexts, have been examined in vitro; these studies argue that a structural transition associated with increased length occurs to mediate aggregation Perutz et al. Trends Biochem. Sci. 24:58–63, 1999).

SUMMARY

The present invention is based, in part, on the discovery of methods for identifying compounds that mediate (by promoting or inhibiting) protein-protein interaction (e.g., aggregation, dimerization, or other physiologially significant association). For example, the methods can be used to identify compounds that inhibit, in cells, the aggregation of complexes that include glutamine-rich polypeptides. Compounds that mediate such interaction, which are also within the scope of the invention, can be used to treat Alzheimer's disease, disorders associated with expanded CAG repeats (such as Huntington's disease), and disorders in which polyglutamine—containing transcription factors or coactivators are undesirably active (e.g., disorders associated with homodimerization of jun or hexamerization of p53).

In one embodiment, the method is carried out by obtaining a cell that expresses a fusion protein that contains a fluorescent polypeptide (e.g., a fusion protein that contains a fluorescent polypeptide and a glutamine-rich polypeptide; the fluorescent polypeptide can be a polypeptide that naturally fluoresces or a non-fluorescent polypeptide that is labeled with a fluorescent tag), exposing the cell to a compound, incubating the cell with the compound, and assessing the fluorescence emitted by the fluorescent polypeptide. An increase in the fluorescence emitted by the fluorescent polypeptide (following incubation of the cell with the compound) indicates that the compound inhibits the interaction (e.g. aggregation) of polypeptides (e.g., glutamine-rich polypeptides). Conversely, a decrease in the fluorescence emitted indicates that the compound promotes interaction.

To most accurately assess the compound, the fluorescence emitted by the fluorescent polypeptide will be assessed just after the cell has been exposed to the compound (i.e., before any significant incubation has occurred) as well as after the period of incubation. When the method is carried out in this way, the first reading will more accurately reflect the background fluorescence by taking into account any fluorescence emitted by the compound per se. Of course, less accurate measurements could be obtained in other ways (e.g. by assessing background fluorescence before the compound is added to the cell). In this method, as well as the others described herein, the compound can be virtually any substance (e.g., the compound can be a biological molecule, such as a polypeptide expressed in the cell, a chemical compound, or a small molecule). Libraries that encode or contain candidate compounds are available to those of ordinary skill in the art through charitable sources (e.g., ChemBridge Corporation (which provides useful information about chemical libraries on the worldwide web) and commercial suppliers.

A "glutamine-rich polypeptide" is a polypeptide having 26 or more consecutive amino acid residues (e.g. 33, 34, 35, 36, 37, 40, 42, 47, 50, 52, 60, 65, 70, 72, 75, 80, 85, 95, 100, 103, 104, 110, 119, 120, 130, 140, 144, 151, 160, 170, 180, 190, 191, 195, 200, 210, 230, 250, 270 or 300 glutamine residues). Polypeptides having such a region of consecutive glutamine residues may also be referred to as having an extended polyglutamine or polyQ region. Glutamine-rich polypeptides may be naturally occurring polypeptides such as the huntingtin protein, atrophin-1, ataxin-1, ataxin-2, ataxin-3, the α1a-voltage dependent calcium channel, ataxin-7, the androgen receptor, alpha, beta, and gamma syncleins, those involved in amyloidosis, such as those with immunoglobulin light chains, amyloid-associated protein, mutant transthyretin, beta2 microglobulin, beta2 amyloid protein, and the prion proteins. The terms "protein," "peptide," and "polypeptide" are used herein to refer to any chain of amino acid residues.

The cells that can be used in the methods described herein can be mammalian cells (e.g., the cell of a rodent, non-human primate, or human) or yeast cells (of any strain). Regardless of the cell type used, the fusion proteins they express can be placed under the control of an inducible promoter. Many useful inducible promoters are known in the art. For example, in the event yeast cells are employed, they can express a fusion protein under the control of a Gal1 promoter.

In addition to the glutamine-rich polypeptide and the fluorescent polypeptide, the fusion protein can include an N-terminal amino acid sequence consisting of 5–35 (e.g., 5, 8, 10, 12, 15, 18, 20, 23, 27, 29, 31, or 35) amino acid residues. This sequence can be a fragment of any existing protein or a random sequence. The N-terminal amino acid sequence can also be the FLAG-tag sequence.

In another embodiment, the invention features methods for identifying a compound that promotes the interaction (e.g., aggregation) of polypeptides, including glutamine-rich polypeptides, by obtaining a cell that expresses a fusion protein that includes the polypeptide (e.g., a glutamine-rich polypeptide), exposing the cell to the compound, and assessing the growth rate of the cell. An increase in the growth rate of the cell indicates that the compound inhibits the interaction of the polypeptides. Conversely, suppression of growth indicates that the compound stimulates or promotes the interaction of the polypeptides. In this embodiment and the others described herein, the polypeptides whose aggregation is in question can be identical to one another or they may differ from one another.

The methods of the invention can also be used to identify a gene product that mediates interaction of glutamine-rich polypeptides (i.e., a gene product that, possibly in concert with other gene products, functions to either promote or inhibit the association of polypeptides, including glutamine-rich polypeptides). Gene products, which serve as targets for therapeutic agents, can be identified in assays in which fluorescence, cell growth, or both, are assessed. For example, a gene product that mediates the interaction between glutamine-rich polypeptides can be identified by obtaining a mutant yeast cell that expresses a glutamine-rich polypeptide and assessing the rate of growth of the cell. An increase in the rate of growth, relative to that of a wild type yeast cell that expresses the glutamine-rich polypeptide indicates that the gene product that is mutant in the yeast cell is a gene product that mediates aggregation of glutamine-rich polypeptides. Alternatively, where a fluorescence-based assay is used, a gene product that mediates interaction of glutamine-rich polypeptides can be identified by obtaining a mutant yeast cell that expresses fusion protein that includes a glutamine-rich polypeptide and a fluorescent polypeptide, exposing the cell to the compound, incubating the cell with the compound, and assessing the fluorescence emitted by the fluorescent polypeptide. An increase in fluorescence, relative to that of a wild type yeast cell that expresses the glutamine-rich polypeptide, indicates that the gene product that is mutant in the yeast cell is a gene product that mediates aggregation of glutamine-rich polypeptides.

Another method that can be used to identify a target for a therapeutic agent is carried out by obtaining cells that express a fusion protein that includes a polypeptide (e.g., a polypeptide prone to aggregation, perhaps in the context of a disease process (e.g., a glutamine-rich polypeptide)), transfecting the cells with an expression library of mammalian genes, and assessing the growth of the cells. An alteration in the growth of a cell (among those transfected and relative to non-transfected cells) indicates that that cell has been transfected with a mammalian gene that mediates aggregation of the polypeptide (e.g. the glutamine-rich polypeptide). Therefore, the gene, or the gene's product, is a target for a therapeutic agent that mediates the aggregation of glutamine-rich polypeptides. Here again, the method can be fluorescence based, in which case the cell would express a fusion protein that includes a glutamine-rich polypeptide and a fluorescent polypeptide, and fluorescent emission, rather than cell growth, would be assessed.

The use of a fluorescent marker is convenient, but other markers can be used as well. In any of the methods described herein, a non-fluorescent polypeptide can be substituted for the fluorescent polypeptide. Those of ordinary skill in the art will recognize that many non-fluorescent polypeptides can be used. For example, the FLAG-tag can be used. When a non-fluorescent polypeptide is used, aggregation of glutamine-rich polypeptides can be assessed by exposing the cell to antibodies that specifically bind the non-fluorescent polypeptide. Of course, the antibodies that specifically bind the non-fluorescent polypeptide can be fluorescently labeled. In any event, while fluorescence can be measured with a device, such as a fluorimeter, it is also possible to detect changes in fluorescence by viewing a labeled cell directly under the microscope. Changes in the size of protein aggregates can be readily apparent to the eye (see, e.g. FIG. 2).

Using the methods of the invention, four compounds have been identified as modulators of polypeptide interaction. Accordingly, these compounds can be used to treat patients who are suffering from Alzheimer's disease, disorders associated with expanded CAG repeats (such as Huntington's disease), or disorders in which polyglutamine-containing transcription factors or coactivators are undesirably active (e.g., disorders associated with homodimerization of jun or hexamerization of p53).

The details of one or more embodiments of the invention are set forth in the accompanying drawings and the description below. Other features, objects, and advantages of the invention will be apparent from the description and drawings, and from the claims.

DETAILED DESCRIPTION

Figure 1:
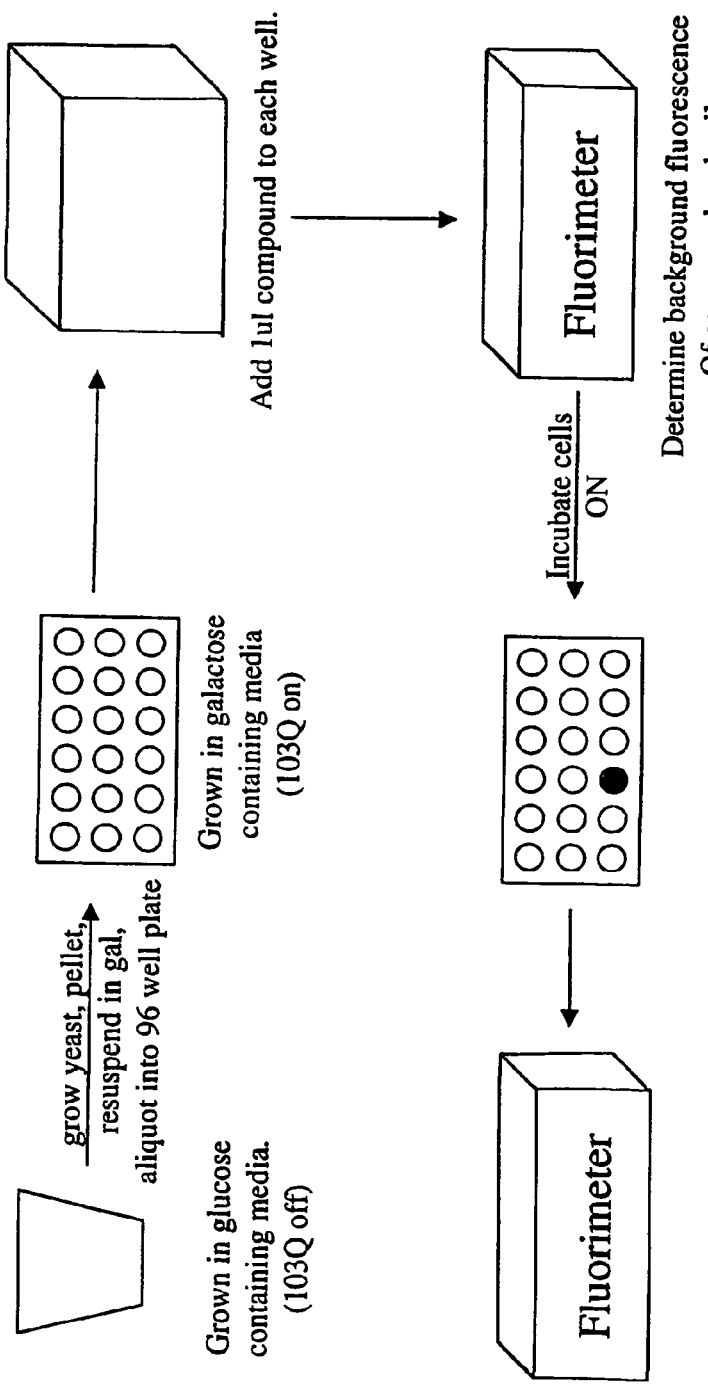
FIG. 1 is a schematic overview of one of the ways the method of the invention can be practiced.
Figure 2:
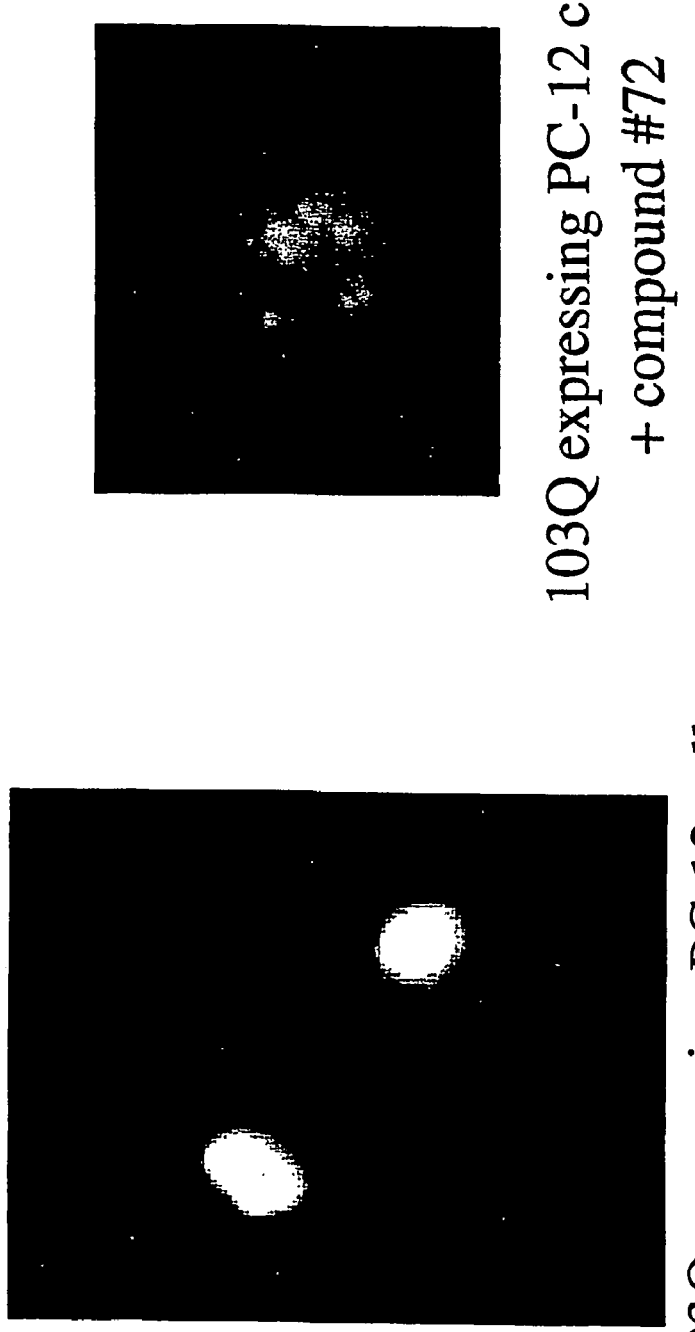
FIG. 2 is a pair of photomicrographs illustrating the fluorescence emitted by PC-12 cells that express a polypeptide having a polyQ repeat of 103 glutamine residues (left-hand photograph) and the fluorescence emitted by analogous PC-12 cells that have been exposed to a compound identified by the methods of the present invention. The compound decreases the size of the aggregates and leads to the formation of multiple aggregates.

The invention features methods that can be used to identify compounds that mediate (by promoting or inhibiting) the association of polypeptides that, when abnormally associated, cause pathological disorders such as Alzheimer's disease, Parkinson's disease, and Huntington's disease. Any polypeptide that, when abnormally associated, causes a pathological disorder, can be used, in whole or in part, in the present methods (as can non-naturally occurring polyQ-containing polypeptides that aggregate). For example, a fragment of a naturally occurring polypeptide containing an extended polyglutamine region or other region that promotes aggregation of the parent protein with copies of itself, or with a different protein, is useful. These polypeptides are referred to herein as glutamine-rich polypeptides or aggregation-disposed polypeptides.

Protein database searches reveal that hundreds of polyQ-containing proteins have been identified to date (see, e.g., Kazantsev et al., *Proc. Natl. Acad. Sci. USA* 96:11404–11409, 1999). Examples of naturally occurring aggregation-disposed polypeptides include those having extended polyglutamine regions: huntingtin (which is associated with Huntington's disease); atrophin-1 (which is associated with dentatorubralpallidoluysian atrophy); ataxin-1 (which is associated with spinocerebellar ataxia type 1); ataxin-2 (which is associated with spinocerebellar ataxia type-2); ataxin-3 (which is associated with spinocerebellar ataxia type 3); alpha 1a-voltage dependent calcium channel (which is associated with spinocerebellar ataxia type-6); ataxin-7 (which is associated with spinocerebellar ataxia type-7); and the androgen receptors (which are associated with spinobulbar muscular atrophy). Other useful naturally occurring polypeptides are the synuclein proteins (alpha, beta, and gamma synuclein). Synucleins have been implicated in Alzheimer's disease, Parkinson's disease and breast cancer. Proteins such as amyloid light chains and amyloid-associated proteins, which are associated with amyloidosis, can also be used in the methods of the invention. Other aggregation-disposed polypeptides include: mutant transthyretin, which is associated with familial amyloid polyneuropathies; beta2 microglobulin, aggregation of which causes complications during chronic renal dialysis; beta amyloid protein, which is associated with Alzheimer's disease; immunoglobulin light chain, which is associated with multiple myelomas and various other B-cell proliferations; and prion proteins, which cause spongiform encephalopathies like Creutzfeldt-Jakob disease and kuru in humans.

Non-naturally occurring, aggregation-disposed polypeptides include variants of naturally occurring polypeptides, as well as polypeptides which do not occur in nature but have the ability to aggregate, particularly where such polypeptides can be used to model naturally-occurring, disease-associated proteins such as huntingtin and beta amyloid protein. These include polypeptides that are engineered to include regions known to promote polypeptide aggregation.

Both naturally occurring and non-naturally occurring aggregation-disposed polypeptides can be produced recombinantly. Of course, recombinant methods can be used to fuse other proteins (e.g. heterologous proteins) to aggregation-disposed polypeptides. For example, the glutamine-rich polypeptide can be fused to an antigenic tag, such as c-myc or FLAG-tag, or a proteinaceous label such as a green fluorescent protein (GFP, which term includes enhanced GFP, or "EGFP"). The cell in which the recombinant polypeptide is produced can be used directly in the methods of the invention, or the recombinant polypeptide can be purified from the culture medium or from a lysate of the cells.

Variants of the aggregation-disposed polypeptides can also be used in the methods of the invention and can be prepared by substituting selected amino acid residues in these polypeptides. A variant of an aggregation-disposed polypeptide includes a polypeptide that has high sequence identity (e.g., 60, 70, 80, 90, 95, 96, 97, 98, or 99%) to an aggregation-disposed polypeptide and retains the ability to aggregate.

Isolated nucleic acid molecules that encode naturally occurring, aggregation-disposed polypeptides, variants thereof, or non-naturally occurring aggregation-disposed polypeptides are useful in the methods of the invention. Naturally occurring nucleic acid sequences that encode aggregation-disposed polypeptides are well known in the art and can be obtained, for example, from GENBANK™. The nucleic acid triplet that encodes the amino acid glutamine can be either CAA or CAG. The CAA or CAG codons need not be present in equal numbers and need not form a repeating pattern.

Typically, expressing an aggregation-disposed polypeptide in a cell involves inserting an aggregation-disposed polypeptide coding sequence into a vector, where it is operably linked to one or more expression control sequences. The need for, and identity of expression control sequences will vary according to the type of cell in which the aggregation-disposed polypeptide sequence is to be expressed. Examples of expression control sequences include transcriptional promoters, enhancers, suitable mRNA ribosomal binding sites, and sequences that terminate transcription and translation.

Suitable expression control sequences can be selected by one of ordinary skill in the art. Standard methods can be used by the skilled person to construct expression vectors. See, generally, Sambrook et al., 1989, *Cloning—A Laboratory Manual* ($2^{nd}$ Ed), Cold Spring Harbor Laboratory Press, Cold Spring Harbor, N.Y.

Vectors useful in this invention include plasmid vectors and viral vectors. Viral vectors can be, for example, those derived from retroviruses, adenoviruses, adeno-associated virus, SV40 virus, pox viruses, or herpes viruses. Once introduced into a host cell (e.g., a bacterial cell, a yeast cell, an insect cell, an avian cell, or a mammalian cell), the vector can remain episomal, or be incorporated into the genome of the host cell. Useful vectors include vectors that can be purchased commercially, e.g., pcDNA 3.1-based vectors can be purchased from Invitrogen (Carlsbad, Calif.).

The aggregation-disposed polypeptides can be chemically coupled to a label or recombinantly expressed as a fusion protein with a label. Examples of labels include various enzymes, fluorescent materials, luminescent materials, and bioluminescent materials. Examples of suitable enzymes include horseradish peroxidase, alkaline phosphatase, β-galactosidase, and acetylcholinesterase; examples of suitable fluorescent materials include umbelliferone, fluorescein, fluorescein isothiocyantate, rhodamine, dichlorotriazinylamine fluorescein, dansyl chloride, phycoerythrin, green fluorescent protein, and blue fluorescent protein; an example of a luminescent material is luminol; examples of bioluminescent materials include luciferase, luciferin, and aequorin; and examples of suitable radioactive materials include $^{125}$I, $^{131}$I, $^{35}$S, $^{32}$P, and $^{3}$H.

The coupling of a label to the aggregation-disposed polypeptide can be carried out by chemical methods known in the art.

Fluorescence can be detected by any method known in the art (e.g., using fluorescent microscopy, a fluorometer, or fluorescence-activated cell sorting).

Figure 4:
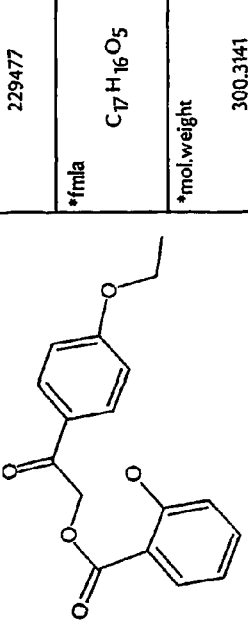
FIG. 4 is a drawing of a compound identified by the methods of the invention that strongly inhibits the interaction of glutamine-rich polypeptides.
Figure 6:
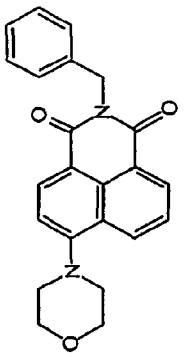
FIG. 6 is a drawing of a compound identified by the methods of the invention.
Figure 3:
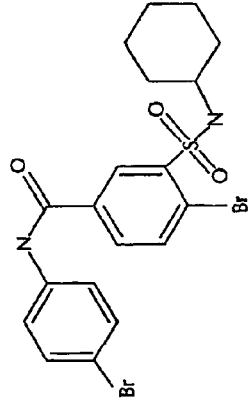
FIG. 3 is a drawing of a compound identified by the methods of the invention that strongly inhibits the interaction of glutamine-rich polypeptides.
Figure 5:
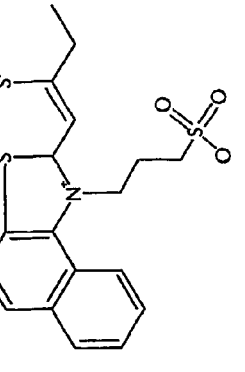
FIG. 5 is a drawing of a compound identified by the methods of the invention that weakly inhibits the interaction of glutamine-rich polypeptides.

The compounds identified by the methods described herein (which may also be referred to herein as "therapeutic agents"), and particularly those shown in FIGS. 3–6, can be used to treat a variety of disorders (including Alzheimer's Disease and the other disorders named above), including Huntington's disease. Huntington's disease (HD) is an autosomal dominant and progressive neurodegenerative disorder. It is associated with selective neuronal cell death that occurs primarily in the cortex and striatum and is characterized by a movement disorder, cognitive deficits, and psychiatric symptoms. HD is caused by an expansion of a CAG codon repeat in the first exon of the huntingtin (htt) gene, which encodes a 350 kDa protein of unknown function (Ambrose et al., *Somat. Cell Mol. Genet.* 20:27–38, 1994). The nucleotide triplet CAG encodes the amino acid glutamine ("Gln" or "Q"). Thus, CAG repeats encode polyglutamine regions within huntingtin (and wherever they occur). The polyglutamine region of huntingtin from non-HD individuals contains about 8–31 consecutive glutamine residues. When the protein has more then 37 consecutive glutamine residues, mild to severe HD results. The more severe cases of the disease exhibit up to about 68 glutamine residues. A juvenile onset form of HD is characterized by more widespread neuronal degeneration and is caused by expansions above approximately 65 repeats.

The invention also features use of the compounds described herein for the preparation of a medicament for the treatment of Alzheimer's Disease, Huntington's Disease, and the other aggregation-mediated conditions described herein.

In addition to HD, at least seven other inherited neurodegenerative disorders are associated with CAG expansions. Increasing the length of CAG repeats in the coding regions of unrelated genes, and resulting polyglutamine regions in the encoded proteins, causes a similar pattern of neuron degeneration, indicating a similar, if not identical, mechanism of cell death. This cell death may be caused by abnormal protein-protein interactions mediated by elongated polyglutamines. Thus, each of the neurodegenerative disorders associated with CAG expansions are amenable to treatment with the therapeutic agents of the present invention.

The therapeutic agents of the invention are not, however, limited to the treatment of neurodegenerative disorders. The therapeutic agents of the invention can be used to treat any disease, disorder, or condition that results from an abnormal or undesirable association between two polypeptides (like or unlike). For example, the therapeutic agents of the invention can be used to treat Alzheimer's disease (by inhibiting the association of tau proteins) and disorders in which polyglutamine-containing transcription factors or coactivators are undesirably active (e.g. disorders (e.g., cancers) associated with homodimerization of jun or hexamerization of p53).

"Treatment" encompasses administration of a therapeutic agent as a prophylactic measure to prevent the occurrence of disease or to lessen the severity or duration of the symptoms associated with the disease. Physicians and others of ordinary skill in the art routinely make determinations as to the success or failure of a treatment. Treatment can be deemed successful despite the fact that not every symptom of the disease is totally eradicated.

It is usual in the course of developing a therapeutic agent that tests of that agent in vitro or in cell culture are followed by tests in animal models of human disease, and further, by clinical trials for safety and efficacy in humans. Accepted animal models for many diseases are now known to those of ordinary skill in the art. For example, therapeutic agents of the present invention can be screened in a *Drosophila* model of neurodegeneration.

Mammalian models for Huntington's disease are also available. To generate these models, the Hd protein homolog is first cloned from the genome of the selected mammal using standard techniques. For example, the sequence can be amplified by PCR or obtained by screening an appropriate library under conditions of low stringency (as described, e.g., in Sambrook et al. supra.). Subsequently, CAG repeats are introduced into the HD gene by molecular cloning and mutagenesis techniques. The site for insertion of the repeat sequence can be located by alignment of the HD cDNA from the desired mammal with the human cDNA for HD. The modified HD gene with artificially expanded repeats is reintroduced into the mammal using standard methods for transgenesis.

If the desired animal model is a mouse, numerous models of HD are available (see, e.g., U.S. Pat. No. 5,849,995; for a review, see Chicurel et al., Expression of Huntington's Disease Mutation in Mice at hdfoundation.org/PDF/hdmicetable(.pdf) (2000). The mouse HD cDNA sequence is deposited in GenBank as L23312 and L23313. Methods for generating transgenic mice are routine in the art (See, e.g., Hogan et al., *Manipulating the Mouse Embryo*, Cold Spring Harbor Laboratory Press, Cold Spring Harbor, N.Y. (1994)). A mouse bearing a transgene comprising the HD gene and expanded CAG repeats has symptoms similar to the human disease. Murine symptoms can include hyperactivity, circling, abnormal gait, tremors, learning deficits, hypoactivity, and hypokinesis. Neuropathological symptoms include general brain atrophy, progressive striatal atrophy, neuropil aggregates, inclusions in the striatum, reduced dendritic spines, cell loss in the cortex, and striatum. Any of these behavioral or physiological deficits can be assessed in order to determine the efficacy of a given therapeutic agent of the invention. For example, the agent can be administered to a transgenic mouse model, generated as described above. The symptoms of a treated mouse can be compared to untreated mice at various times during and after treatment. In addition, treated and untreated mice can be sacrificed at various intervals after treatment, and the neuropathology of the brain can be analyzed. Thus, the efficacy of the treatment can be evaluated readily by comparing the behavioral symptoms, neuropathological symptoms, and clinical symptoms of treated and untreated mice.

The therapeutic agents of the invention can be administered alone, or in a mixture, in the presence of a pharmaceutically acceptable excipient or carrier (e.g., physiological saline). The excipient or carrier is selected on the basis of the mode and route of administration. Suitable pharmaceutical carriers, as well as pharmaceutical necessities for use in pharmaceutical formulations, are described in *Remington's Pharmaceutical Sciences* (E. W. Martin), a well known reference text in this field, and in the USP/NF (United States Pharmacopeia and the National Formularly).

A pharmaceutical composition (e.g., a composition containing a therapeutic agent or the DNA molecule encoding it) is formulated to be compatible with its intended route of administration. Examples of routes of administration include oral, rectal, and parenteral, for example, intravenous, intradermal, and subcutaneous, transdermal (topical), and transmucosal, administration.

In treating neurodegenerative disorders, or other disorders within the central nervous system, with therapeutic agents of the invention, the agents must contact the affected neurons (e.g., neurons of the cortex and striatum) to provide a therapeutic effect. If the agents are provided orally or parenterally (e.g., intravenously), rather than locally, the agents must be either permeable to the blood-brain barrier or be assisted in traversing it.

The blood-brain barrier is an obstacle for the delivery of drugs from circulation in the bloodstream to the brain. The endothelial cells of brain capillaries are connected by tight intercellular junctions, which inhibit the passive movement of compounds out of the blood plasma into the brain. These cells also have reduced pinocytic vescicles in order to restrict the indiscriminate transport of materials intracellularly. These features of the brain regulate the exchange of materials between plasma and the central nervous system. Both active and passive transport mechanisms operate to exclude certain molecules from traversing the barrier. For example, lipophilic compounds are more permeable to the barrier than hydrophilic compounds (Goldstein et al., *Scientific American* 255:74–83, 1996; Pardridge et al., *Endrocrin. Rev.* 7:314–330, 1996).

However, the blood-brain barrier must also allow for the selective transport of desired materials into the brain in order to nourish the central nervous system and to remove waste products. The mechanisms by which this is accomplished can provide the means for supplying the therapeutic agents described herein.

Therapeutic agents of the invention can be delivered to the CNS following conjugation with other compounds as follows (and as described further in U.S. Pat. No. 5,994,392). In one instance, polar groups on a drug are masked to generate a derivative with enhanced lipophilic qualities. For example, norepinephrine and dopamine have been modified with diacetyl and triacetyl esters to mask hydroxyl groups. An implementation of this strategy has been previously used to create a pro-drug derivative of dopamine (see U.S. Pat. No. 5,994,392). The modified drugs are generally referred to as pro-drugs. This method has the additional advantage of providing an inactive species of the drug in general circulation. Thus, the pro-drug is able to cross the blood-brain barrier. Subsequently, enzymes present in the central nervous system are able to hydrolyze the ester linkages, thereby liberating the active drug. Thus, therapeutic agents of the invention are chemically modified to create pro-drugs by, e.g., conjugation to a lipophilic moiety or carrier. A compound or derivative thereof, having at least one free hydroxyl or amino group, can be coupled to a desired carrier. The carrier can be a fatty acid, a steroid, or another lipophilic moiety.

For example, the hydroxyl groups are first protected with acetonide. The protected agent is then reacted with the desired carrier in the presence of a water-extracting compound (e.g., dicyclohexyl carbodiiamide), in a solvent (e.g., dioxane, tetrahydrofurane), or N,N dimethylformamide at room temperature. The solvent is then removed, and the product is extracted using methods routinely used by those of ordinary skill in the art. Amine groups can be coupled to a carboxyl group in the desired carrier. An amide bond is formed with an acid chloride or low carbon ester derivative of the carrier. Bond formation is accompanied by HCl and alcohol liberation. Alcohol groups on the drug compound can be coupled to a desired carrier using ester bonds by forming an anhydride derivative, i.e. the acid chloride derivative, of the carrier. One of ordinary skill in the art of chemistry will recognize that phophoramide, sulfate, sulfonate, phosphate, and urethane couplings are also useful for coupling a therapeutic agent to a desired carrier.

Procedures for delivering therapeutic agents of the invention to the CNS can also be carried out using the transferrin receptor as described, for example, in U.S. Pat. No. 6,015,555. To implement this procedure, the agents are conjugated to a molecule that specifically binds to the transferrin receptor (e.g., an antibody or fragment thereof, or transferring. Methods for obtaining antibodies against the transferrin receptor and for coupling the antibodies to a desired drug are also described in U.S. Pat. No. 6,015,555.

Monoclonal antibodies that specifically bind to the transferrin receptor include OX-26, T58/30, and B3/25 (Omary et al., *Nature* 286:888–891, 1980), T56/14 (Gatter et al., *J. Clin. Path.* 36:539–545, 1983), OKT-9 (Sutherland et al., *Proc. Natl. Acad. Sci. USA* 78:4515–4519, 1981), L5.1 (Rovera, *Blood* 59:671–678, 1982) and 5E-9 (Haynes et al., *J. Immunol.* 127:347–351, 1981). In one embodiment, the monoclonal antibody OX-26 is used. The antibody of choice can be an Fab fragment, a $F(ab')_2$ fragment, a humanized antibody, a chimeric antibody, or a single chain antibody.

The antibody to the transferrin receptor is conjugated to a desired therapeutic agent of the invention with either a cleavable, or non-cleavable linker. The preferred type of linker can be determined without undue experimentation by making cleavable and non-cleavable conjugates and assaying their activity in, for example, an in vitro or cell culture assay described herein. Examples of chemical systems for generating non-cleavable linkers include the carbodiimide, periodate, sulfhydryl-maleimide, and N-succinimidyl-3-(2-puridyldithio) propionate (SPDP) systems. Carbodiimide activates carboxylic acid groups, which then react with an amino group to generate a noncleavable amide bond. This reaction is useful for coupling two proteins. Periodate is used to activate an aldehyde on an oligocacharide group such that it can react with an amino group to generate a stable conjugate. Alternatively, a hydrazide derivative of the desired compound can be reacted with the antibody oxidized with periodate. Sulfhydryl-maleimide and SDPD use sulfhydryl chemistry to generate non-cleavable bonds. SDPD is a heterobifunctional crosslinker that introduces thiol-reactive groups. In the sulfhydryl-maleimide system, an NHS ester (e.g., gamma-maleimidobutyric acid NHS ester) is used to generate maleimide derivative, for example, of a protein drug or antibody. The maleimide derivative can react with a free sulfhydryl group on the other molecule.

Cleavable linkers are also useful. Cleavable linkers include acid labile linkers such as cis-aconitic acid, cis-carboxylic alkadienes, cis-carboxylic alkatrienes, and polypeptide-maleic anhydrides (see U.S. Pat. No. 5,144,011).

In a preferred embodiment, the therapeutic agent of the invention is a tri-domain polypeptide. Such a polypeptide can be covalently attached to an antibody specific for the transferrin receptor. The coupling can be made by fusing a gene encoding the therapeutic polypeptide to a gene encoding a monoclonal antibody specific for the transferrin receptor. The gene encoding the monoclonal antibody can obtained using polymerase chain reaction strategies to amplify the gene from hybridoma cells (see, e.g., Orlandi et al., *Proc. Natl. Acad. Sci. USA* 86:3833–3837, 1989; Larrick et al., *Bio/technology* 7:934–938, 1989; Gavilondo et al., *Hybridoma* 9:407–417, 1990). PCR primers are designed to anneal to the leader sequence, or the first framework region of the antibody variable domain and to the J region or the constant region. The PCR primers are used to amplify the immunoglobulin gene from cDNA or genomic DNA of the hybridoma. The amplification product is cloned into an expression vector or a cloning vector. The antibody can also be humanized, modified to be a single chain antibody, a chimera, or other derivatives known in the art. In one embodiment, construction of a single chain antibody is preferred in order to facilitate covalent fusion with the polypeptide agent, for example, a tri-domain therapeutic polypeptide.

The cloned antibody gene is fused to a covalent linker attached to the polypeptide agent of the invention. These features can be inserted using synthetic oligonucleotides, standard cloning procedures, and PCR. They can be amino- or carboxy-terminal to the antibody gene. Oligonucleotides and restriction sites for cloning are selected such that the linker and the desired polypeptide compound are inserted in frame with respect to the antibody coding sequence. Moreover, a protease recognition site can be included in the linker if cleavage of the antibody is required after delivery. The resulting fusion gene can be inserted into an expression vector as appropriate, and the fusion protein can be produced, for example, in *E. coli*, insect cells, and mammalian cells in tissue culture. Alternatively, the fusion gene can be inserted into a gene therapy vector for expression in a subject.

Therapeutic polypeptides can also be modified by lipidation in order to stabilize the polypeptide and to promote traversal of the blood-brain barrier. A method for lipidation of antibodies is described by Cruikshank et al. (*J. Acquired Immune Deficiency Syndromes and Human Retrovirology* 14:193, 1997).

The efficacy of strategies to deliver a desired compound across the blood-brain barrier can, of course, be monitored. The desired agent, conjugated for delivery across the blood-brain barrier, is administered to a test mammal (e.g., a rat, a mouse, a non-human primate, a cow, a dog, a rabbit, a cat, or a sheep). One of ordinary skill in the art will, however, recognize that the permeability of the blood-brain barrier varies from species to species, with the human blood-brain barrier being the least permeable. The mode of administration can be the same as the desired mode of treatment, or it can be intravenous. For a comprehensive analysis, a set of test mammals is used. The test mammals are sacrificed at various times after the agent is administered and are then perfused through the heart with Dulbecco's phosphate-buffered saline (DPBS) to clear the blood from all organs. The brain is removed, frozen in liquid nitrogen, and subsequently sectioned in a cryostat. The sections are placed on glass microscope slides. The presence of the desired agent is then detected in the section, for example with an antibody, or by having administered a radiolabeled or otherwise tagged compound (such labeled polypeptide agents are described above). Detection is indicative of the compound having successfully traversed the blood-brain barrier. If a method of enhancing the compounds permeablility to the blood-brain barrier is being assessed, then the amount of the agent detected in a brain section can be compared to the amount detected in a brain section from an animal treated with the same compound without the enhancing method.

The terms "blood-brain barrier permeant" or "blood-brain barrier permeable" are qualities of a compound for which the ratio of a compound's distribution at equilibrium in the cerebrospinal fluid (CSF) relative to its distribution in the plasma (CSF/plasma ratio) is greater than 0.01, generally at least 0.02, preferably at least 0.05, and most preferably at least 0.1.

Where the therapeutic agent is a polypeptide, it can be encoded by an isolated DNA molecule. These DNA molecules can be inserted into a variety of DNA constructs and vectors for the purposes of gene therapy. As used herein, a "vector" is a nucleic acid molecule competent to transport another nucleic acid molecule to which it has been covalently linked. Vectors include plasmids, cosmids, artificial chromosomes, and viral elements. The vector can be competent to replicate in a host cell or to integrate into a host DNA. Viral vectors include, for example, replication defective retroviruses, adenoviruses and adeno-associated viruses. A gene therapy vector is a vector designed for administration to a subject, for example, a mammal (such as a human), such that a cell of the subject is able to express a therapeutic gene contained in the vector.

The gene therapy vector can contain regulatory elements (e.g., a 5' regulatory element, an enhancer, a promoter, a 5' untranslated region, a signal sequence, a 3' untranslated region, a polyadenylation site, and a 3' regulatory region). For example, the 5' regulatory element, enhancer, or promoter can regulate transcription of the DNA encoding the therapeutic polypeptide. The regulation can be tissue specific. For example, the regulation can restrict transcription of the desired gene to brain cells (e.g., cortical neurons or glial cells); hematopoietic cells; or endothelial cells. Alternatively, regulatory elements can be included that respond to an exogenous drug, for example, a steroid, tetracycline, or the like. Thus, the level and timing of expression of the therapeutic polypeptide can be controlled.

Gene therapy vectors can be prepared for delivery as naked nucleic acid, as a component of a virus, or of an inactivated virus, or as the contents of a liposome or other delivery vehicle. Alternatively, the gene delivery agent, for example, a viral vector, can be produced from recombinant cells that produce the gene delivery system. Appropriate viral vectors include retroviruses, for example, Moloney retrovirus, adenoviruses, adeno-associated viruses, and lentiviruses, for example, Herpes simplex viruses (HSV). HSV is potentially useful for infecting nervous system cells.

A gene therapy vector can be administered to a subject, for example, by intravenous injection, by local administration (see U.S. Pat. No. 5,328,470) or by stereotactic injection (see e.g., Chen et al., Proc. Natl. Acad. Sci. USA 91:3054–3057, 1994). The gene therapy agent can be further formulated, for example, to delay or prolong the release of the agent by means of a slow release matrix. One preferred method of providing a recombinant therapeutic polypeptide, is by inserting a gene therapy vector into bone marrow cells harvested from a subject. The cells are infected, for example, with a retroviral gene therapy vector, and grown in culture. Meanwhile, the subject is irradiated to deplete the subject of bone marrow cells. The bone marrow of the subject is then replenished with the infected culture cells. The subject is monitored for recovery and for production of the therapeutic polypeptide.

An appropriate dosage of the therapeutic agents of the invention must be determined. An effective amount of a therapeutic molecule is the amount or dose required to ameliorate a symptom of a disorder associated with trinucleotide repeat expansion, Alzheimer's disease, or cancers associated with the dimerization or other association of transcriptional regulators. Determining the amount required to treat a subject is routine to one of ordinary skill in the art (e.g., a physician, pharmacist, or researcher). First, the toxicity and therapeutic efficacy of an agent (i.e. a tri-domain molecule) is determined. Routine protocols are available for determining the $LD_{50}$ (the dose lethal to 50% of the population) and the $ED_{50}$ (the dose therapeutically effective in 50% of the population) in non-human animals. The therapeutic index is measured as the ratio of the $LD_{50}/ED_{50}$. Compounds, formulations, and methods of administration with high therapeutic indices are preferable as such treatments have little toxicity at dosages that provide high efficacy. Compounds with toxic or undesirable side effects can be used, if means are available to deliver the compound to the affected tissue, while minimizing damage to unaffected tissue.

In formulating a dosage range for use in humans, the effective does of tri-domain compound can be estimated from in vitro cell studies and in vivo studies with animal models. If an effective dose is determine for ameliorating a symptom in cell culture, a dose can be formulated in an animal in order to achieve a circulating plasma concentration of sodium butyrate that falls in this range. An exemplary dose produces a plasma concentration that exceeds the $IC_{50}$ (i.e., the concentration of the test compound which achieves a half-maximal inhibition of symptoms) as determined in cell culture assays. The circulating plasma concentration can be determined, for example, by administering a labeled therapeutic composition to the test animal, obtaining a blood sample, and quantitating the amount of labeled compound present at various times after administration.

An appropriate daily dose of a tri-domain therapeutic can be between about 0.1 mg/kg of body weight to about 500 mg/kg, or between about 1 mg/kg to about 100 mg/kg. The dose can be adjusted in accordance with the blood-brain barrier permeability of the compound. For example, a polypeptide such as an antibody can be administered at a dosage of 50 mg/kg to 100 mg/kg in order to treat the brain. The dose for a patient can be optimized while the patient is under care of a physician, pharmacist, or researcher. For example, a relatively low dose of a tri-domain therapeutic can be administered initially. The patient can be monitored for symptoms of the disorder being treated (e.g., HD). The dose can be increased until an appropriate response is obtained. In addition, the specific dose level for any particular subject can vary depending on the age, body weight, general health, gender, and diet of the subject, the time of administration, the route of administration, the rate of excretion, and other drugs provided in combination.

The efficacy of a dose of any therapeutic agent can be determined in a subject. For example, the subject can be monitored for clinical symptoms, for example, a symptom of a trinucleotide repeat disease, such as a symptom of HD. Behavioral symptoms of HD include irritability, apathy, lethargy, depression, hostile outbursts, loss of memory and/or judgment, loss of ability to concentrate, anxiety, slurred speech, difficulty swallowing and/or eating, and inability to recognize persons. Clinical symptoms of HD include loss of coordination, loss of balance, inability to walk, uncontrolled movements of the fingers, feet, face, and/or trunk, rapid twitching, tremors, chorea, rigidity, and akinesia (severe rigidity).

A number of embodiments of the invention have been described. Nevertheless, it will be understood that various modifications may be made without departing from the spirit and scope of the invention.

An assay carried out with yeast cells and a fluorescent marker: Fragments of huntingtin gene with expanded polyglutamine (104Q) and with polyglutamine of normal length (25Q) were expressed in yeast S. cereviciae. The genes for 104Q and 25Q were fused to the DNA sequence encloding green fluorescent protein to allow microscopic detection of the corresponding polypeptide in vivo. Also, both genes contained a short sequence corresponding to FLAG-tag at the N-termini. 104Q and 25Q were expressed in yeast under the regulation of a Gal1 promoter. Upon transfer of the cells to a galactose-containing medium, 104Q formed multiple aggregates (10–20 per cell) in the cytoplasm within 4–6 hours, while 25Q was soluble. 25Q-GFP had no effect on the growth rate of the cells. In contrast, 104Q expression caused a general cessation of growth. With time, expression of 104Q strongly declined and yeast growth was partially restored, but at a very low rate. The presence of FLAG-tag in the 104Q sequence may be critical for growth cessation.

A screen for genes that modulate the toxicity of polyQ-containing polypeptides and formation of inclusion bodies: The following screen for yeast genes that are involved in the process of polyQ aggregation and in the polyQ-dependent growth defect was based on the growth defect. We selected a number of mutant clones expressing 104Q, which formed large colonies (i.e. clones in which the growth defect was suppressed). In some of these colonies, aggregation of 104Q was strongly inhibited, while in others, aggregation was normal. Three clones that demonstrated suppressed aggregation were analyzed. About 85% of cells in these clones did not have inclusion bodies at all, while 15% of cells had one large aggregate. Interestingly, expression levels of 104Q in these mutants were much higher than in the parental wild type, and reached the levels of expression of 25Q. Increased expression of 104Q in the mutants closely correlated with increased fluorescence. Mutations in these clones were identified by complementation and appeared to be in the HSP104 gene. Precise deletion of the gene hsp 104 also led to suppression of the growth defect caused by 104Q, prevented aggregation of this polypeptide, and allowed its high expression. Mutations in ssa1,2 and ydj1 genes also affected 104Q aggregation but had very different phenotypes. There were many more inclusion bodies in these mutants, but they were much smaller than in the wild type, and the fraction of 104Q in these inclusion bodies was very low. Similar to hsp 104 mutation, ssa1,2 and ydj1 mutations that reduced formation of inclusion bodies also suppressed growth defect caused by the extended polyQ domain. Based on these data, we have established a simple screen for mammalian genes that inhibit formation of aggregates when overexpressed. An expression library of mammalian genes from HeLa cells was transfected into 104Q-GFP-expressing yeast cells and large clones (i.e., those in which growth defect was suppressed), were selected. We have screened about 30,000 colonies, and we picked 21 colonies that demonstrated suppression of growth defect. Many of the plasmids were "false positives," since they were unable to suppress growth defect after isolation and re-transforming into a different 104Q-expressing clone. Some of the plasmids were "false positives" because they suppressed growth defect by reducing expression of 104Q. However, two plasmids, each present in several selected clones, encoding mammalian genes partially suppressed 104Q aggregation. These plasmids caused phenotypes similar to mutants in Hsp70 and DnaJ genes. Sequencing of these genes showed that one of them was a chaperonin TCP1α and another one was an unknown ORF. This genetic approach will allow dissecting the mechanisms of formation of inclusion bodies, and will identify potential targets for design of drugs that affect aggregation of polyQ-containing proteins, as well as other proteins.

Screening of chemical compound libraries: Two major phenotypical differences between cells expressing 104Q and 25Q (i.e., difference in growth rate and in fluorescence) allowed us to establish screen for chemical compounds that affect aggregation. Microtiter plates were adopted to screen chemical libraries by the described method. Yeast, which carry 104Q-, and 25Q-encoding plasmids grew in a liquid medium in the presence of glucose, which inhibits polyQ expression. In the mid-log phase of growth, cells were washed to remove glucose and were resuspended in a medium containing galactose, which induces polyQ expression. The cell suspensions were placed in 96- or 348-well plates and incubated with aeration at 30° C. for 20 hours. Cell density and fluorescence were then measured using a plate reader. Very little increase in the culture density and fluorescence was seen with cells expressing 104Q, but with 25Q-expressing cells, both parameters increased strongly. In general, about 3–5 fold difference in cell number, and about 20–30 fold difference in fluorescence between 104Q and 25Q cultures was detected. Compounds from a chemical library were added to 104Q culture right after plating into the microtiter plates. Compounds that enhanced cell growth or fluorescence were selected. These compounds were then tested for the ability to reduce aggregation of 104Q. We obtained 13 compounds that either enhanced growth or reduced aggregation of cells expressing 104Q, or did both. These compounds were then tested for the ability to reduce aggregation of 104Q in cells of the neuron-derived cell line PC12. The compounds screened out by this method can be used as leads for development of drugs for treatment of diseases related to expansion of polyQ.

The protocol for using an epitope tagged polyQ peptide in lieu of an EGFP fusion: (1) plate cells on uv-treated cover slips in 2 cm 6× well plate and incubate over night in 2 ml 10% serum containing DME media; (2) next day, transiently transfect the cells with 1–2 mg of DNA plasmid encoding myc tagged polyQ using the lipofection reagent, Transfectam, following the Promega standard protocol; (3) after 48 hours, wash the cells twice in PBS, fix them in 2% formaldehyde for 10 minutes, treat them for five minutes with 0.1% Triton-X (this would permeabilize the cells), then incubate them in a humidified chamber with PBS with 10% goat serum and 0.2% Tween-20; (4) visualize the cells with an anti-myc fluorescent antibody (Cy3, rhodamine and FITC are commonly used fluorophores, FLAG, myc and HA are common epitope tags); and (5) analyze inhibition of aggregation, using high magnification fluorescent microscopy.

What is claimed is:

1. A method for identifying a compound that inhibits the aggregation of glutamine-rich polypeptides, the method comprising:

obtaining a cell that expresses a fusion protein comprising a glutamine-rich polypeptide and a fluorescent polypeptide;

exposing the cell to the compound;

measuring the fluorescence emitted by the cell for a first time;

incubating the cell with the compound; and measuring the fluorescence emitted by the cell for a second time, wherein an increase in the fluorescence emitted by the cell the second time, relative to the first time, indicates that the compound inhibits the aggregation of glutamine-rich polypeptides.

* * * * *